United States Patent
Sawyer et al.

(10) Patent No.: US 6,861,255 B1
(45) Date of Patent: Mar. 1, 2005

(54) METHOD OF USING FISH PLASMA COMPONENTS FOR TISSUE CULTURE

(75) Inventors: Evelyn S. Sawyer, Freeport, ME (US); Paul A. Janmey, Media, PA (US); Lisa A. Flanagan, Brookline, MA (US)

(73) Assignee: Sea Run Holdings, Inc., Freeport, ME (US)

( * ) Notice: Subject to any disclaimer, the term of this patent is extended or adjusted under 35 U.S.C. 154(b) by 83 days.

(21) Appl. No.: 10/418,189

(22) Filed: Apr. 17, 2003

Related U.S. Application Data (63) Continuation-in-part of application No. 09/907,443, filed on Jul. 18, 2001, now Pat. No. 6,599,740.

(51) Int. Cl.[7] .............................. C12N 5/02; C12N 5/06
(52) U.S. Cl. ....................... 435/325; 435/368; 435/404; 435/405; 435/406; 435/407; 435/408
(58) Field of Search .................................. 435/325, 368, 435/404, 405, 406, 407, 408

(56) References Cited

U.S. PATENT DOCUMENTS 5,426,045 A * 6/1995 Sawyer et al. ............... 435/392
5,443,984 A * 8/1995 Sawyer et al. ............... 435/392

* cited by examiner

*Primary Examiner*—David Guzo
(74) *Attorney, Agent, or Firm*—IP Strategies (57) ABSTRACT

A process of using a fish plasma component as a nutrient medium component for tissue culture includes obtaining blood from a fish that is a progeny of domesticated broodstock that are reared under consistent and reproducible conditions, separating plasma from the blood, and extracting one or more specific components of the plasma. The tissue is cultured using the extracted plasma components, and none of any remainder of the plasma, in a nutrient medium. The tissue cultured using the extracted plasma component is other than fish tissue, such as mammalian tissue or insect tissue.

21 Claims, 8 Drawing Sheets

Bovine fibrin gels

METHOD OF USING FISH PLASMA COMPONENTS FOR TISSUE CULTURE

CROSS-REFERENCE TO RELATED APPLICATION

This is a continuation-in-part of U.S. patent application Ser. No. 09/907,443, filed on Jul. 18, 2001, now U.S. Pat. No. 6,599,740.

FIELD OF THE INVENTION

The present invention relates generally to the culture of tissue, including cells and organs, and more specifically to the culture of mammalian tissue using at least one component of plasma derived from fish. The method has significant advantages over the more commonly used technique of utilizing serum or plasma components derived from humans or cows, or the more recently developed technique of utilizing whole serum or plasma from fish.

BACKGROUND OF THE INVENTION

Tissue culture, the production of living tissue in vitro, permits numerous applications that would be difficult or impossible in a living organism. These applications include in vitro applications such as diagnosing disease and assessing toxicity, and more recently, the production of therapeutics, including vaccines and recombinant proteins, and growing human tissue, including cells and organs, for therapeutic applications (tissue engineering).

The culture of animal tissue usually requires animal biologics: either whole serum, most commonly fetal calf serum (FBS), or plasma components, for "serum-free" media or biological gels. Current methods for deriving mammalian serum or plasma components are well-known. The raw material is human or bovine blood from which the cellular portion is removed by centrifugation. If an anticoagulant is used, the liquid portion is plasma; if the blood is allowed to clot, the liquid portion is serum. The most widely used method of fractionating human or bovine plasma is the Cohn process (Cohn et al., 1946), which utilizes adjustments of temperature, pH, and ethanol to separate plasma proteins.

However, the risk of the presence of mammalian infectious organisms in mammalian plasma or serum products used in tissue culture for therapeutics is an increasing concern. Some plasma proteins can be manufactured by recombinant technology, others, especially the glycoprotcins, must be obtained from humans or animals. Although various viral-inactivation treatments for plasma or serum components are frequently used, problems remain in achieving 100% inactivation without compromising quality. An even more serious concern is the emergence of transmissible spongiform encephalopathies (TSEs) such as "mad cow disease", and the possibility of prions or infectious proteins in plasma or serum derivatives. The later problem is especially difficult, since at present, it is not possible to predict which individual blood donors, human or bovine, may years later develop a prion disease.

In order to improve the safety profile of animal products used in mammalian cell culture, Sawyer et al. (U.S. Pat. Nos. 5,426,045 and 5,443,984) developed a method using fish whole serum to replace FBS or other animal serum. This fish serum provided the important advantage of a low probability of mammalian infectious agents, and successfully replaced FBS by promoting growth in a few cell lines. However, it was toxic to many mammalian cells, and ineffective for others.

Sawyer et al., in the '045 patent, identified (among several factors) the high lipid content of fish serum as "potentially inhibiting" to mammalian cell growth. Therefore, we attempted to overcome the toxicity problem by removing some of the lipid.

Using known methods (Condie, 1979: Ando, 1996), we separated lipids and lipoproteins from the plasma of Atlantic salmon (Salmo salar). The delipidated plasma was used to replace FBS on several mammalian cell lines. In each case, the material proved toxic to the mammalian cells.

This toxicity pointed to a similar problem with the removed lipid. Furthermore, cell culture teaches a like-to-like match or species-specificity of biological materials used and cells being cultured (Hewlett, 1991). Since fish lipids are significantly different from mammalian lipids (Babin and Vernier, 1989), it seemed unlikely that the fish lipid would promote mammalian cell growth. Nonetheless, we tried the salmon lipid as a media supplement for a mammalian cell line (Vero). The unexpected result was enhanced growth of the mammalian cells.

Because of the success of the lipid component, we attempted to overcome whole plasma toxicity by separating (purifying) other components from the whole plasma, in particular, plasma proteins, which might be useful in mammalian tissue culture. This approach presented the problem of dissimilar structure between fish and mammalian plasma proteins, and therefore a low probability that a given protein would function in a similar manner to its mammalian homologue. Doolittle (1987) studied fish plasma proteins from the perspective of comparative physiology and evolution, and found only partial identity in amino acid sequence to their mammalian homologues. For example, lamprey fibrinogen is less than 50% homologous to human fibrinogen, and salmon transferrin has only a 40–44% amino acid sequence identity with human transferrin (Denovan-Wright, 1996). This and similar data on percent homology for other plasma proteins such as fish albumin (28% homology) would dissuade those skilled in mammalian cell culture from attempting to use the fish homologue.

We encountered additional difficulties since the usual method of fractionating mammalian plasma protein (Cohn et al., 1946) could not be used with salmon plasma. The Cohn process is the most widely used method of separating, or fractionating, serum or plasma into its components. Although this process has been improved and modified considerably, it achieves basic separation and precipitation of plasma fractions by cold temperature, and adjustments in pH and ethanol concentration. Since the temperature of salmon blood is often 4° C. or less when it is drawn from the fish during winter, temperature separation of proteins was not a consistent or reliable method.

Figure 1:
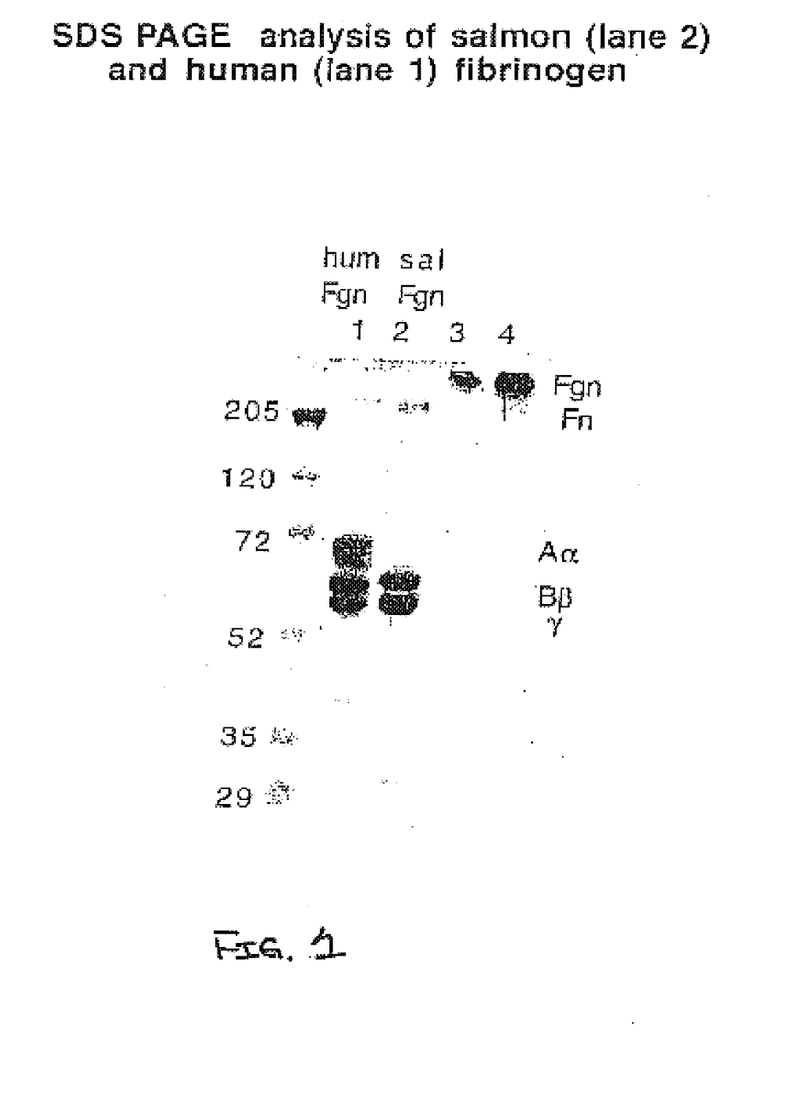
FIG. 1 shows an SDS-PAGE analysis of primary structures of human (lane 1) and salmon (lane 2) fibrinogen.

Sawyer et al. (U.S. Pat. No. 6,007,811) extracted two proteins, fibrinogen and thrombin, from salmon plasma for use as a sealant for hemostasis. However, immunoblots and SDS-PAGE showed a different primary structure for human (lane 1.) vs. salmon (lane 2.) fibrinogen (FIG. 1). Furthermore, this application is unrelated to cell culture, and provided no indication that these proteins would be less cytotoxic than the salmon whole plasma.

Fibrinogen and thrombin form a fibrin gel, and an optimal environment for certain mammalian cells, especially neurons, is a three-dimensional matrix, usually a gel made from mammalian proteins. We used methods known for mammalian plasma to purify fibrinogen and thrombin from salmon plasma. We chose mouse spinal cord neurons as test cells for the fish fibrin gel, since they are a model for human neuron regeneration, and very sensitive to toxicity.

Figure 2:
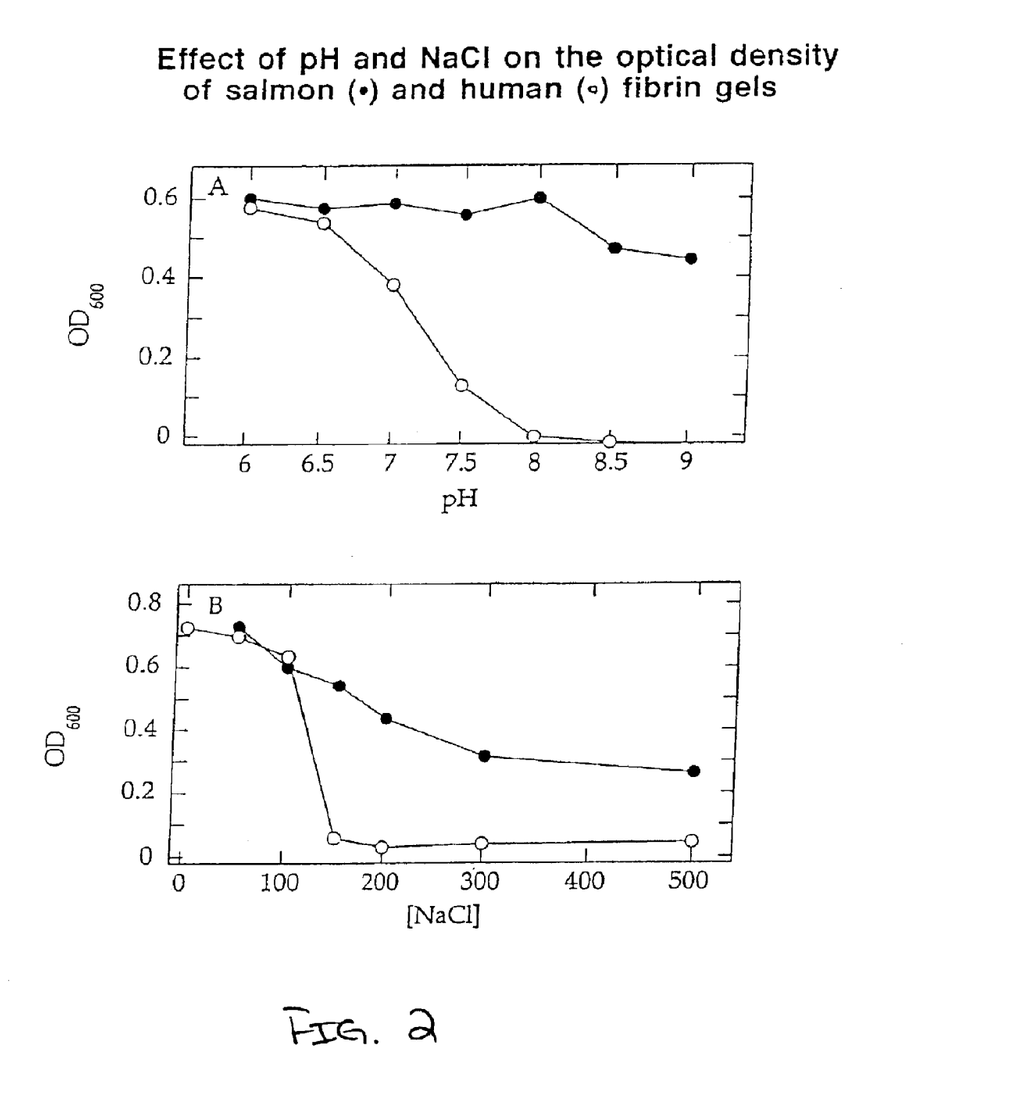
FIG. 2 illustrates the resistance to changes in pH and osmolality of salmon fibrin gel.

When the survival and process outgrowth of these neurons was compared in human, bovine, and salmon fibrin gels, the unexpected result was the superior performance of the neurons in the fish material. Since mammalian fibrin gels are already being used to grow neurons for therapeutic purposes, the improved neuron process outgrowth and safety profile of the fish gels would make them an attractive alternative. Additional advantages of the salmon gel were its ease of preparation (lyophilized salmon fibrinogen can be resolublized at room temperature instead of at 37° C.), and resistance to changes in pH and osmolality (FIG. 2).

SUMMARY OF THE INVENTION

The present invention overcomes the cytotoxicity of fish whole serum or plasma, provides material with unique, advantageous properties for cell culture, and retains the important safety profile of fish biologics over the more commonly used serum or plasma components derived from humans or cows.

According to an exemplary aspect of the invention, a process of using a fish plasma component in a nutrient medium for tissue culture includes obtaining a fish that is a progeny of domesticated broodstock that are reared under consistent and reproducible conditions, and obtaining blood from the fish. Plasma is separated from the blood, and one or more specific components of the plasma are extracted. Mammalian stem cell tissue is cultured using the one or more extracted plasma components, and none of any remainder of the plasma, in a nutrient medium.

According to the foregoing process, the fish can be a cold water fish, such as a Salmonid, for example, an Atlantic salmon. The one or more specific components of the plasma can include, for example, fibrinogen, thrombin, lipids, transferrin, albumin, plasma proteins, and enzymes, alone or in combination. According to a particular embodiment, the one or more specific components of the plasma are fibrinogen and thrombin, and culturing tissue using the extracted plasma components, and none of any remainder of the plasma, in a nutrient medium, includes preparing a gel with the fibrinogen, the thrombin, and calcium in tissue culture media. In this case, culturing tissue further includes embedding the stem cell tissue in the gel.

According to the process of the invention, the mammalian stem cell tissue can be human stem cell tissue. In general, the mammalian stem cell tissue can be, for example, neural stem cell tissue, embryonic stem cell tissue, or hematopoetic stem cell tissue, alone or in combination.

Extracting the one or more components from the plasma can include performing an extraction process on the plasma such that all process temperatures are no greater than 4° C., no cytotoxic chemical residues remain in the one or more plasma components, and no oxidation of plasma lipids occurs.

The fish from which the blood is obtained can be at least one of the following: sexually immature, in the log-phase of growth, larger than two kilograms, and reared by standard husbandry methods.

Obtaining blood from the fish can include rendering the fish to a level of loss of reflex activity, and drawing blood from a caudal blood vessel. Prior to rendering the fish to a level of loss of reflex activity, the levels of proteolytic enzymes and non-protein nitrogen present in the blood of the fish can be reduced.

Separating plasma from the blood can include centrifuging the blood. The process of the invention can also include adding an antioxidant to the plasma prior to extracting the one or more specific components of the plasma. Culturing tissue in the one or more extracted plasma components can include seeding the tissue in a defined medium and the one or more extracted plasma components.

DETAILED DESCRIPTION OF THE INVENTION

Because of the many risks and uncertainties inherent in human and other mammalian biologics, and the cytotoxicity and ineffectiveness of fish whole serum or plasma, the method of the present invention uses fish plasma components that are separated (purified) from the whole plasma of farmed fish, which can be used in culturing mammalian tissue. Fish species for which consistent and reproducible methods of production are well established are suited for use in the method of the present invention. Exemplary use of salmonids, specifically the Atlantic salmon (Salmo salar), will be described and demonstrated; however, the scope of the present invention is not limited to use of this particular species.

In addition to the advantage of relative safety, the substances (fractions) derived from salmon plasma enhance growth of certain mammalian cells. However, fish plasma components are not conventionally used, and are actually discouraged for use in mammalian cell culture for several reasons, including:

1. Fish whole serum or plasma has failed to supplement or replace FBS in the media used for mammalian cell culture due to the frequent toxicity and ineffectiveness of the fish material.
2. Fish are traditionally considered to be free-ranging, wild animals. Therefore, apparent uncertainty in quality, availability, and reproducibility of their blood products would seem to make them unsuitable donors.
3. The usual, and most cost-effective, method of fractionating human or other mammalian serum or plasma proteins (Cohn process) is not suitable for salmon or other coldwater fish, since the separation depends in part on temperature effects. Since salmon plasma can vary in temperature from 0° C. to 16° C. seasonally, this method is unreliable.
4. Conventional cell culture teaches a like-to-like match or species-specificity of biological materials in the culture media, and cells being cultured (Hewlett, 1991). For example, Hewlett cautions against the use of lipoproteins from other than human or bovine sources for human cells due to species-specificity. Likewise, fish serum is recommended over bovine serum for the culture of (RTG2) rainbow trout gonadal cells (DeKoning and Kaattari, 1992).

5. Fish plasma proteins have been studied from the perspective of comparative physiology and evolution, and found only partially identical to their mammalian homologues (Doolittle, 1987). For example, salmon transferrin has only a 40–44% amino acid sequence identity with human transferrin (Denovan-Wright et al., 1996). This and similar data for other plasma proteins such as fish albumin (Davidson et al., 1989) would dissuade those skilled in the field of mammalian cell culture from trying fish proteins.

6. Compared to plasma from mammals, salmon and trout plasma contain oxidative enzymes that remain active at low temperatures, and therefore are likely to generate cytotoxic substances. Therefore, special preparation and handling procedures are required.

According to the method of the present invention, each of the cited obstacles has been overcome, and the advantages of the use of fish plasma components are exploited.

The method of the present invention takes advantage of the fact that commercial salmon aquaculture has grown dramatically in the past ten years. In Maine alone, there are over six million fish, averaging 2–4 kilograms each, reared in offshore pens annually. The availability of raw material (blood) and the efficiency of recently developed blood-drawing methods and devices contribute to a large supply and availability of fish blood. By utilizing these domesticated fish stocks reared in aquaculture facilities, plasma can be obtained with product consistency similar to plasma from herds of cattle reared for this purpose.

Further, although amino acid sequences in fish and mammalian plasma proteins have less than 50% identity, many of the critical sequences or active sites required for similar function in both fish and mammals, are highly-conserved among vertebrates including salmon and trout.

Advantages of the present invention include the following:

Salmonid plasma components are unlikely to transmit mammalian infections agents. The wide evolutionary distance between fish and mammals, and the differences in body temperature between mammals and the cold-water fishes such as trout and salmon, provide safety from cross-species infection.

Figure 4:
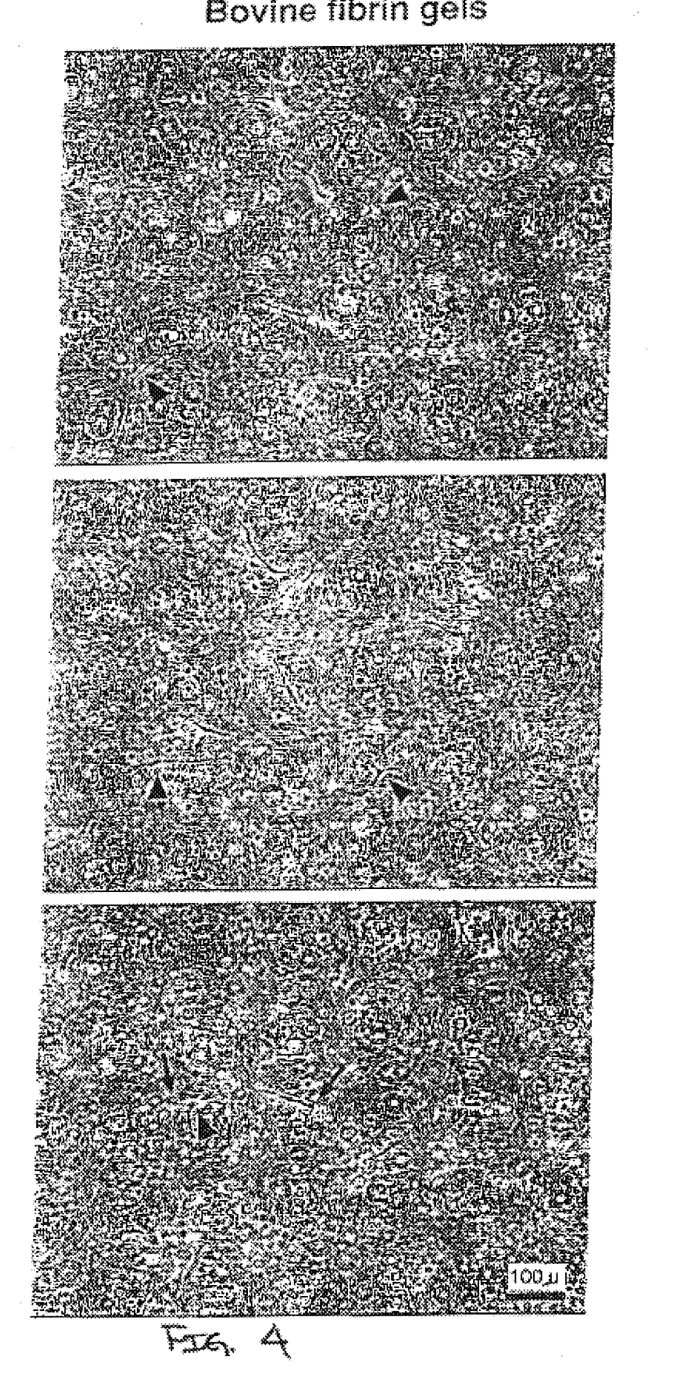
FIG. 4 shows mammalian neurons grown in bovine fibrin gels.
Figure 5:
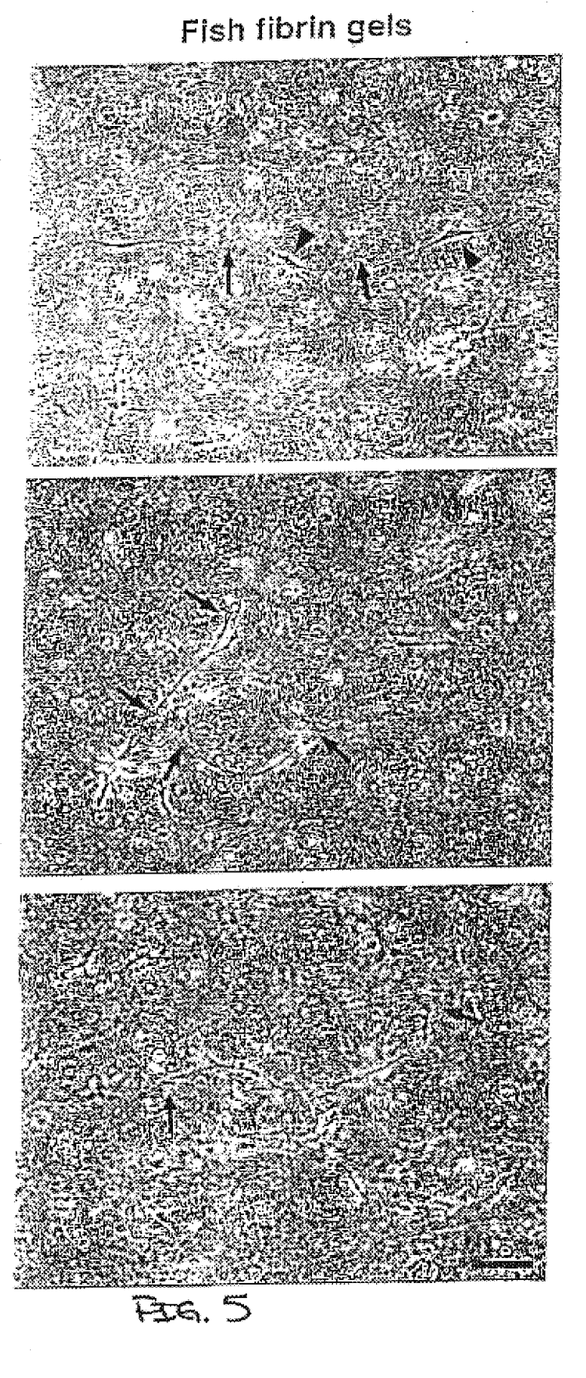
FIG. 5 shows mammalian neurons grown in fish fibrin gels.
Figure 6:
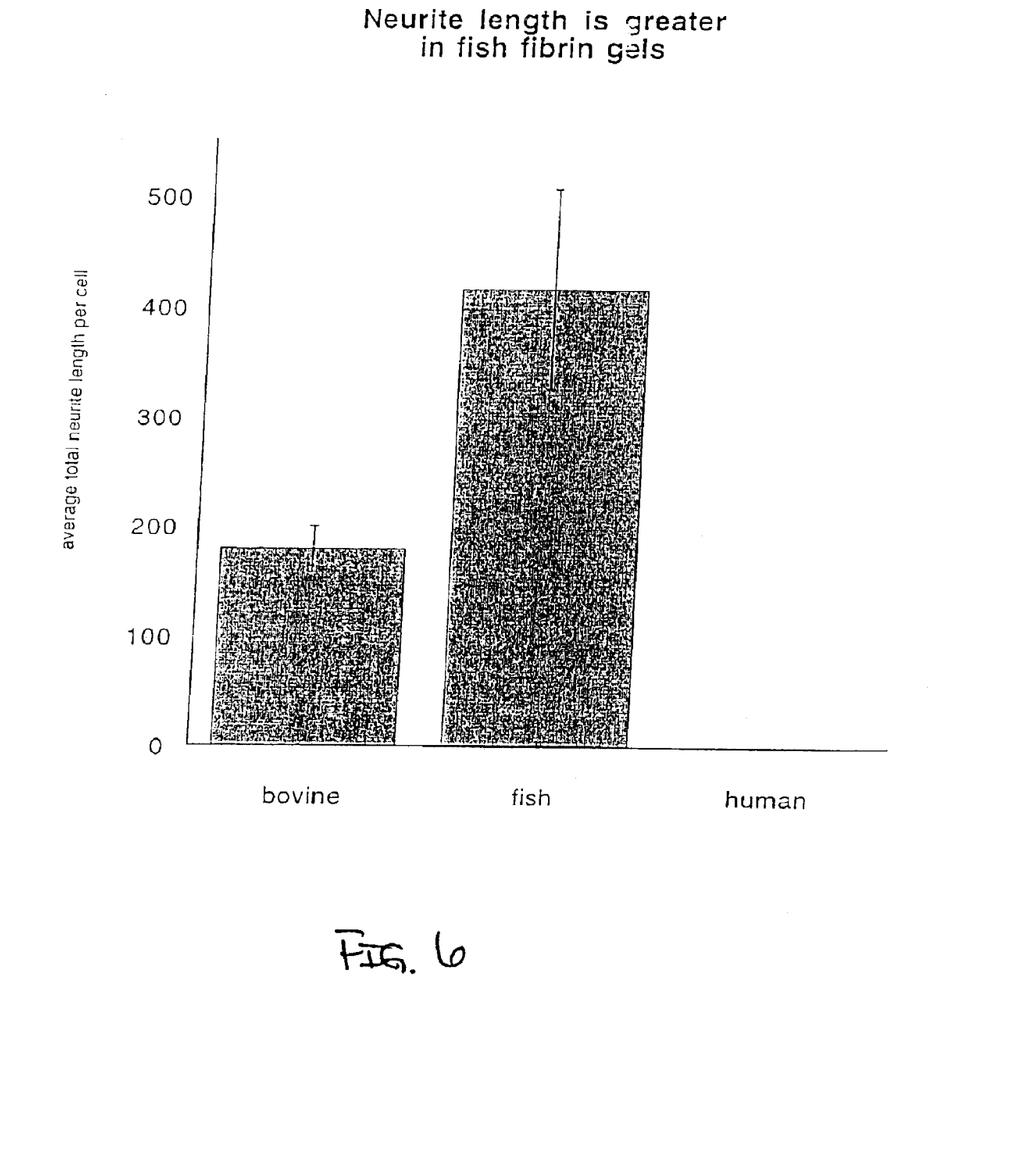
FIG. 6 is a graph depicting the difference in average total neurite length per cell of mammalian neurons grown in bovine fibrin gels and mammalian neurons grown in fish fibrin gels.

Salmonid plasma components are more effective than mammalian products for certain tissue culture applications. Because salmon lipids and plasma proteins must function in vivo over a wide range of temperature, pH, and osmolality, their performance in tissue culture reflects these properties. Salmon lipids are highly unsaturated and rich in omega-3 fatty acids. Lyopholized salmon fibrinogen is easily reconstituted at room temperature, unlike lyophilized mammalian fibrinogens, which must be heated to 37° C. (Catalog 1999, Calbiochem, San Diego, Calif.). Gels produced with salmon fibrinogen and thrombin are more resistant to changes in pH and NaCl concentration than gels made with human proteins (FIG. 2). Mammalian neurons grown in salmon gels show enhanced process outgrowths compared to neurons grown in mammalian gels (FIGS. 4, 5, 6).

Salmonid plasma components can be produced with lot-to-lot consistency. An important requirement is for donor fish to be reared under consistent and reproducible conditions, not necessarily the nature or specifics of these conditions. The reproducibility of conditions reduces variability in quantity and quality of plasma components.

The physiology of fishes, including plasma composition, is regulated to a much greater degree by external factors than that of mammals. Therefore, plasma composition can be manipulated by environmental or nutritional means not possible in mammals. For example, amounts of cholesterol and high-density lipoprotein (HDL) are significantly different in salmon held at different salinities or fed different diets. (Babin and Vernier, 1989).

According to the present invention, the culture of representative mammalian tissue has been demonstrated. The plasma components used were lipids, fibrinogen, and thrombin from the plasma of Atlantic salmon (S. salar). This species was used for the disclosed examples because consistent and reproducible methods for their production are well established, large numbers are reared in commercial aquaculture operations, and individual fish are large enough for blood to be obtained easily. These particular plasma components were chosen because they are plasma fractions frequently used for mammalian cell culture, and serve as examples of other fish plasma components, such as transferrin, albumin, and enzymes, which can also be similarly useful.

Preparation and Extraction

The process begins with the consistent and reproducible conditions under which donor fish are reared. All fish used as plasma sources preferably are progeny of domesticated broodstock, inspected for fish disease according to the American Fisheries Society "Blue Book" standards, sexually immature, in the log-phase of growth, larger than two kilograms, reared by standard husbandry methods, and fed a commercially pelleted food appropriate to the species.

Water temperature at the time of bleeding is preferably 4° C. to 12° C. The fish are preferably starved for five days before bleeding to reduce proteolytic enzymes and non-protein nitrogen. Each fish is stunned, such as by a blow to the head, or by immersion in ice-water, or in water containing $CO_2$ or other fish anesthetic, in order to render the fish to a level of loss of reflex activity (unconsciousness) as defined by Schreck and Moyle, (1990). Whole blood is then drawn, preferably from the caudal artery or vein with a sterile needle and a syringe or vacuum tube containing an anticoagulant such as ACD (acid citrate dextrose), trisodium citrate, or other anticoagulant commonly used in human blood-banking.

Whole blood is held for no more than four hours at 2°–4° C., and then centrifuged at 2°–4° C. Because of the large amounts of highly unsaturated fatty acids, plasma to be used for lipid extraction preferably is handled under argon, or an antioxidant such as alphatocopherol, BHT, or mercaptoethanol at less than 1 ppm is added. Plasma is then frozen, for example, at −80° C.

For plasma lipids, an extraction procedure (for example, that described in detail by Condie, 1979, or Ando, 1996) is applied to whole plasma. In summary, this process utilizes fumed silica to adsorb the lipids from the plasma fraction. Lipids are then eluted from the silica with sodium citrate at pH 10–11 and dialyzed against a saline solution, and additional antioxidants (for example, ascorbic acid, BHA, BHT) are added. The lipid is then analyzed for cholesterol content and concentrated to a level of 5 to 15 mgs/ml cholesterol. The lipid is then stored under vacuum or argon at −80° C.

For fibrinogen extraction and purification, the method of Silver et al., 1995 preferably is used. This method is based on ammonium sulfate precipitations, which yields greater than 95% pure fibrinogen (by SDS-PAGE). Preferably, thrombin is prepared by the method of Ngai and Chang, 1991.

These extraction techniques are illustrative of those currently in use, but other techniques may be equally effective. The essential requirements are that all process temperatures must remain below 4° C., there must be no cytotoxic chemical residues in the product, and plasma lipids must be protected from oxidation.

EXAMPLE #1

Fish Lipids in Tissue Culture

A green monkey kidney cell line (Vero) commonly used in commercial culture, the Promega Nonradioactive Cell Proliferation Assay (Fisher Healthcare, Houston, Tex.), and serum-free media, VP-SFM (Life Technologies, Inc., Grand Island, N.Y.), were used to evaluate the fish lipid component.

Test media were formulated as follows:
1. Control
2. VP-SFM only
3. VP-SFM plus salmon lipid (0.25 mgs/L cholesterol)
4. VP-SFM plus salmon lipid (1.0 mgs/L cholesterol)
5. VP-SFM plus salmon lipid (5.0 mgs/L cholesterol)

The frozen fish lipid was thawed in a water bath at 2–4° C. Assays were conducted using 24-well polystyrene culture plates. Each well was seeded with 30,000 cells in VP-SFM medium containing 5% fetal calf serum (FBS). The cells were allowed to attach and spread for a 24-hour period, and then the growth medium was removed by aspiration. All wells were rinsed thoroughly with the VP-SFM medium and the test formulations (3 wells each) were added.

The cells were then incubated at 37° C. for 48 hours in a 5% $CO_2$ atmosphere in 95% relative humidity.

After 48 hours, the cultures were examined and quantified using the Promega Nonradioactive Cell Proliferation Assay. This assay measures viable cells only and is based on a standard curve of cell concentrations determined for each cell type. Results for each condition were averaged and statistically compared using ANOVA (one-way analysis of variance).

Figure 3:
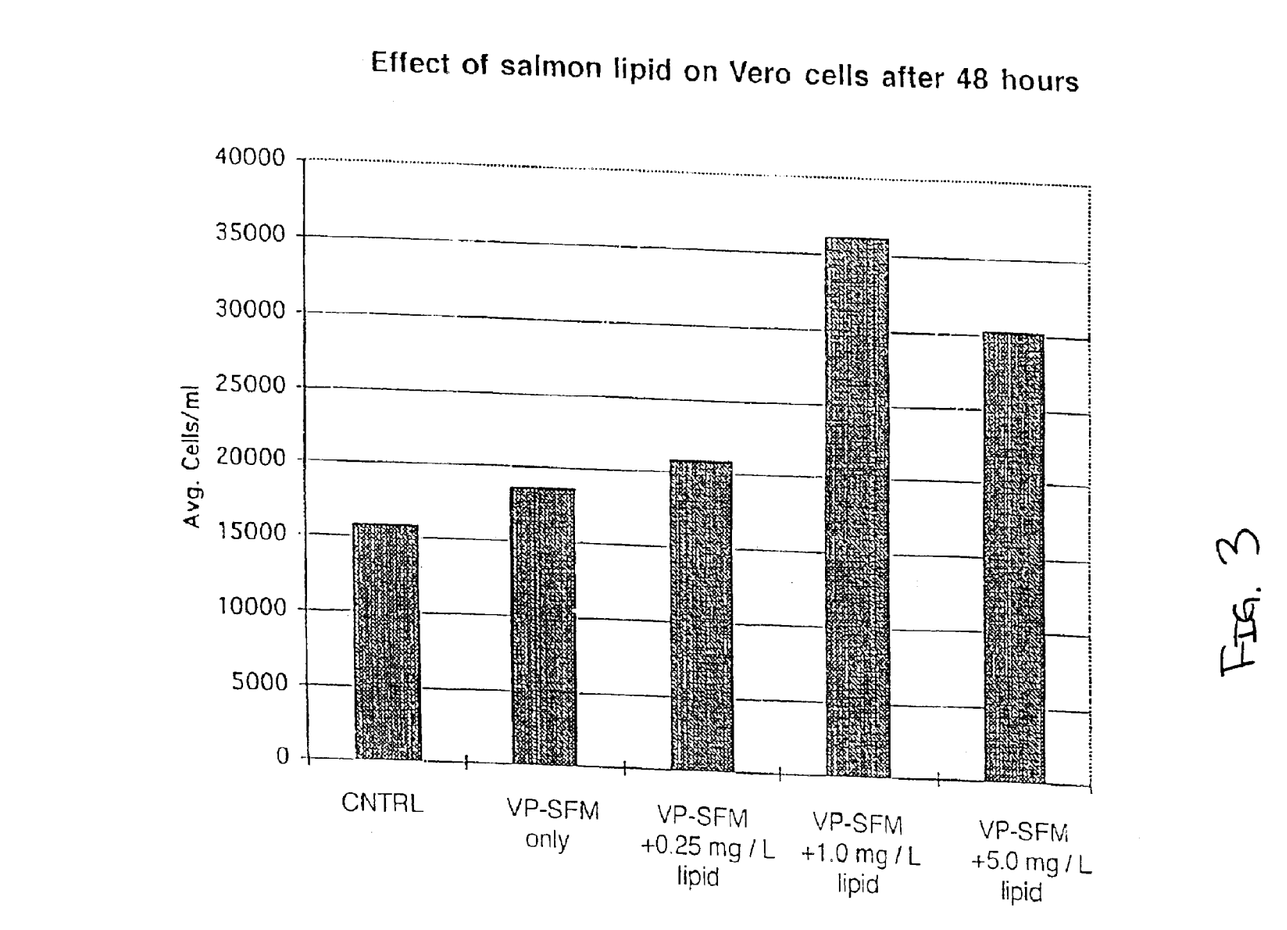
FIG. 3 illustrates the effect of salmon lipid on Vero cells after 48 hours.

There was no significant difference between the number of viable cells in the VP-SFM and the VP-SFM plus the lower concentration of salmon lipid, showing that the fish material was not toxic. However, addition of salmon plasma lipid at the higher concentration to the media (VP-SFM plus 1.0 mgs/L cholesterol) enhanced growth significantly (P=<0.001). The highest concentration of salmon lipid (5.0 mgs/L) was less effective (FIG. 3).

These results show that the salmon plasma lipids enhance the growth of a mammalian cell line (Vero) in culture.

EXAMPLE #2

Neurons in Fish Fibrin Gels

Growing mammalian neurons in a gel made from fish plasma components is an example of in vitro cell culture with potential in vivo (tissue engineering) applications. Cell survival and neurite process extension in gels are established models for nerve regeneration in vivo (Schense et al., 2000).

Primary spinal cord neuronal cultures were prepared as described by Dunham (1988) from embryos harvested from timed-pregnant female mice (C57BL/6J; Jackson Laboratory, Bar Harbor, Me.). Culture media and conditions for the neurons were also as described by Dunham (1988).

Lyophilized salmon fibrinogen and thrombin were reconstituted in water at room temperature, and the gels were prepared by treating 3 mg/L salmon fibrinogen with 1.5 U/ml salmon thrombin and adding 1.4 mM calcium in cell culture media. Similar gels were prepared using lyophilized human and bovine fibrinogen and thrombin. In order to embed neurons in the gel, fibrinogen, neurons, and cell culture media were mixed together, and then thrombin was added. The solution was mixed gently 2–3 times and transferred to a polylysine-coated coverslip. The formation of the fist fibrin gels was similar to gels formed from mammalian material and resulted in a solid gel within 30 minutes at room temperature with a shear modulus of about 550 dynes/cm. After at least 30 minutes, the gels were covered with neuronal cell culture media and placed in a 37° C. cell culture incubator.

The neurons in the fish and mammalian fibrin gels were viewed on a Nikon Diaphot 300 inverted microscope, and images were captured with a Micromax cooled CCD camera driven by Inovision image processing software on a SGI 02 computer. Images were processed and compiled using Adobe Photoshop 5.0. Neurite length was quantified using NIH Image, and all data was analyzed using Kaleidagraph.

After 2 days in culture, human fibrin gels began to disintegrate, and by day 4, the gel was completely digested away, leaving only sparse cells attached to the glass. In contrast, bovine and fish gels remained intact for at least a week. FIGS. 4 and 5 show several examples of neuronal cell bodies (arrowheads) and extended processes (arrows) in the gels. Fish fibrin gels contained multiple neurons with processes longer than those of the neurons in the bovine gels, and extending in three dimensions into the gel. Quantitation of neurite length (microns) in fish gels compared to that in bovine gels reveals that neurite length in fish gels is greater by a factor of 2.3 (fish gels=416.25±89.9 sem, n=10 cells: bovine gels=179.18±20.9 sem, n=8 cells) (FIG. 6).

These results show a clear and significant enhancement of neurite length for mammalian spinal cord neurons when they are cultured in a salmon fibrin gel instead of the mammalian gel.

These experiments demonstrate that those with ordinary skill in the field of tissue culture can substitute fish plasma components for the mammalian plasma substances now used for mammalian tissue culture, and realize significant advantages from the fish material that were not provided by fish whole plasma and serum products. For example, human stem cells have in common the ability to self-renew and differentiate into multiple unique cell types. Recent studies indicate that embryonic, hematopoetic, and neural stem cells share many molecular markers that, as in the case of neural and embryonic stem cells, make them more like each other than like the tissues they differentiate into (Ramalho-Santos et al., 2002; Ivanova et al., 2002). Differentiated cells also often have many characteristics in common despite their diverse functions. For example, cells from organs as disparate as the brain and the pancreas benefit from growth in a deformable three-dimensional matrix such as fibrin (Flanagan et al., 2002; Beattie et al., 2002).

Figure 7:
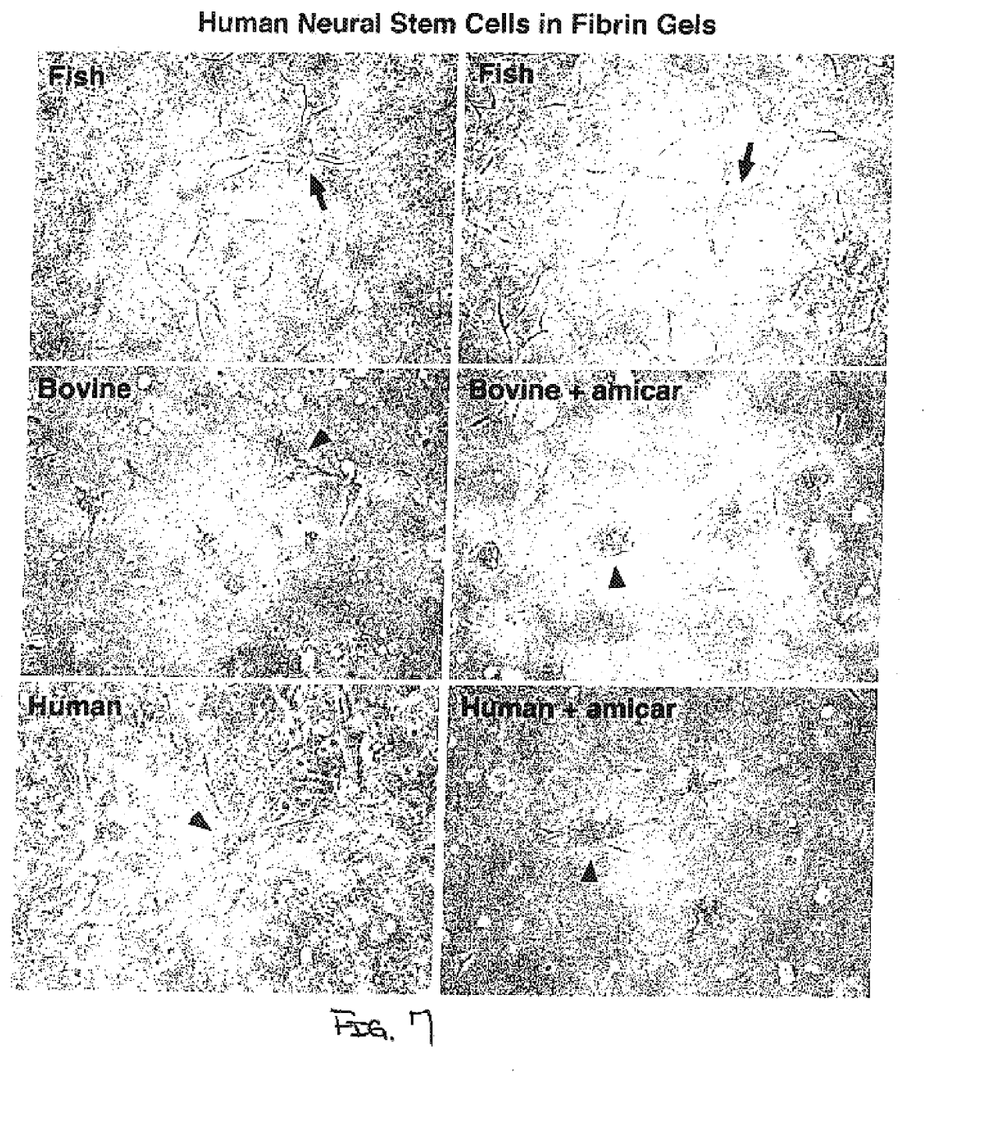
FIG. 7 shows human neural stem cells cultured in various fibrin gels.
Figure 8:
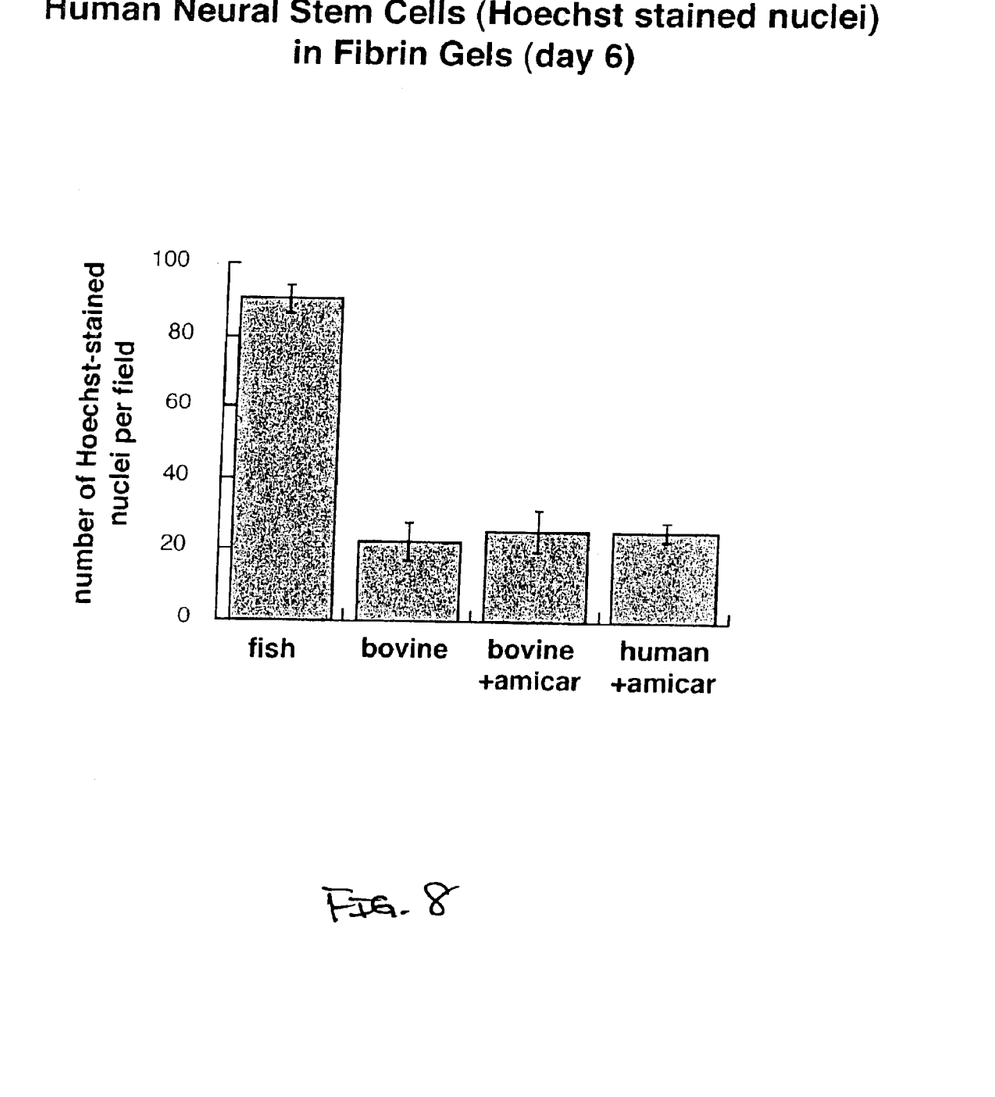
FIG. 8 is a chart showing the number of Hoechst-stained nuclei of human neural stem cells present after six days of culturing in fibrin gels.

FIG. 7 shows several examples of human neural stem cells in fibrin gels, including fish, bovine, and human fibrin gels. FIG. 8 graphs the number of Hoechst-stained human neural stem cell nuclei present in the fibrin gels after six days, for each of four different fibrin gels. As shown, the number of nuclei per field present in the fish gels were far greater than those present in the non-fish gels.

Preferred and alternative embodiments have been described in detail. It is contemplated, however, that various modifications of the disclosed embodiments fall within the spirit and scope of the invention. The scope of the appended claims, therefore should be interpreted to include such modifications, and is not limited to the particular embodiments disclosed herein. For example, the use of these and other fish plasma components in mammalian tissue culture, or fish plasma components in insect cell culture, especially in the production of recombinant proteins, is a contemplated aspect of the present invention to satisfy the same objects and provide the same advantages as those for mammalian cell culture.

REFERENCES

Ando, S. 1996. Adsorbtion of Serum Lipoproteins from Rainbow Trout to Dextran Sulfate Cellulose. Fisheries Science 62 (3): 410–415.

Babin, P. J. and Vernier, J. 1989. Plasma Lipoproteins in Fish. J. Lipid Research 30:467–489.

Beattie et al., 2002. A Novel Approach to Increase Human Islet Cell Mass While Preserving Beta-Cell Function. Diabetes Dec.; 51(12):3435–39.

Cohn, E. J., Strong, L. E., Hughs, W. L., Mulford, D. J., Ashworth, J. N., Melin, M., Taylor, H. L. 1946. Preparation and Properties of Serum and Plasma Proteins IV. A System of Separation Into Fractions of the Protein and Lipoprotein Components of Biological Tissues and Fluids. J. Am. Chem. Soc. 68:459–475.

Condie, R. M. 1979. Preparation of Intravenous Human and Animal Gamma Globulins and Isolation of Albumin. U.S. Pat. No. 4,136,094.

Davidson, W. S., Bartlett, S. E., Birt, T. P., Birt, V. L., Green, J. M. 1989. Identification and Purification of Serum Albumin From Rainbow Trout (Salmo gairdneri). Comp. Biochem. Physiol. 93B (1):5–9.

DeKoning, J., and Kattari, S. 1992. An Improved Lymphocyte Culture Medium Incorporating Plasma for in vitro Antibody Production and Mitogenesis. Fish and Shellfish Immunology 2:275–285.

Denovan-Wright, E. M., Ramsey, N. B., McConnick, C. J., Lazier, C. B., Wright, J. M. 1996. Nucleotide Sequence of Transferrin cDNAs and Tissue Specific Expression of the Transferrin Gene in Atlantic Cod (Gadus Morhua). Compo Biochem: Physiol. 11:3B (2): 269–273.

Doolittle, R. M. 1987. The Evolution of the Vertebrate Plasma Proteins. Biol. Bull. 269–283.

Durham, H. D. 1988. Aggregation of Intermediate Filaments by 2,5-Hexanedione; Comparison of Effects on Neurofilaments, GFAP-Filaments and Vimentin-Filaments in Dissociated Cultures of Mouse Spinal Cord-Dorsal Root Ganglia. J. Neuropathal Exp. Denral. 47(4), 432–442.

Flanagan et al., 2002. Neurite Branching on Deformable Substrates. Neuroreport Dec. 20;13(18):2411–15.

Hewlett, G. 1991. Strategies for Optimising Serum-Free Media. Cytotechnology 5:3–14.

Ivanova et al., 2002. A Stem Cell Molecular Signature. Science Oct. 18;298(5593):601–04.

Ngai, P. K., and Chang, J. Y., 1991. A Novel One-Step Purification of Human Thrombin After Direct Activation of Crude Prothrombin Enriched From Plasma. Biochem J.280:805–808.

Ramalho-Santos et al., 2002. "Stemness": Transcriptional Profiling of Embryonic and Adult Stem Cells. Science Oct. 18;298(5593):597–600.

Schense, J. C., Bloch, J., Aebischer, P., and Hubbell, J. A., 2000. Enzymatic Incorporation of Bioactive Peptides into Fibrin Matrices Enhances Neurite Extension. Nature Biotechnology 18:415–419.

Schreck, C. B. and Moyle, P. B. 1990. Methods for Fish Biology, Am. Fish. Soc. Bethesda, Md.

Silver, F. R. Wang, M. C. and Pins, G. D. 1995. Preparation of Fibrin Glue: A Study of Chemical and Physical Methods. J. Appl. Biomaterials 6(3):175–183.

What is claimed is:

1. A process of using a fish plasma component in a nutrient medium for tissue culture, comprising:
   obtaining a fish that is a progeny of domesticated broodstock that are reared under consistent and reproducible conditions;
   obtaining blood from the fish;
   separating plasma from the blood;
   extracting one or more specific components of the plasma; and
   culturing mammalian stem cell tissue using the one or more extracted plasma components, and none of any remainder of the plasma, in a nutrient medium.

2. The process of claim 1, wherein the fish is a cold water fish.

3. The process of claim 1, wherein the one or more specific components of the plasma include fibrinogen.

4. The process of claim 1, wherein the one or more specific components of the plasma include thrombin.

5. The process of claim 1, wherein the one or more specific components of the plasma include lipids.

6. The process of claim 1, wherein the one or more specific components of the plasma include any of transferrin, albumin, plasma proteins, and enzymes.

7. The process of claim 1, wherein the one or more specific components of the plasma are fibrinogen and thrombin, and
   culturing tissue using the extracted plasma components, and none of any remainder of the plasma, in a nutrient medium, includes preparing a gel with the fibrinogen, the thrombin, and calcium in tissue culture media.

8. The process of claim 1, wherein the mammalian stem cell tissue is human stem cell tissue.

9. The process of claim 1, wherein the mammalian stem cell tissue is neural stem cell tissue.

10. The process of claim 1, wherein the mammalian stem cell tissue is embryonic stem cell tissue.

11. The process of claim 1, wherein the mammalian stem cell tissue is hematopoetic stem cell tissue.

12. The process of claim 1, wherein extracting the one or more components from the plasma includes performing an extraction process on the plasma such that:
   all process temperatures are no greater than 4° C.;
   no cytotoxic chemical residues remain in the one or more plasma components; and
   no oxidation of plasma lipids occurs.

13. The process of claim 1, wherein the fish from which the blood is obtained is at least one of sexually immature, in the log-phase of growth, larger than two kilograms, and reared by standard husbandry methods.

14. The process of claim 1, wherein obtaining blood from the fish includes:
   rendering the fish to a level of loss of reflex activity; and
   drawing blood from a caudal blood vessel.

15. The process of claim 1, wherein separating plasma from the blood includes centrifuging the blood.

16. The process of claim 1, further including adding an antioxidant to the plasma prior to extracting the one or more specific components of the plasma.

17. The process of claim 1, wherein culturing tissue in the one or more extracted plasma components includes seeding the tissue in a defined medium and the one or more extracted plasma components.

18. The process of claim 2, wherein the fish is a salmonid.

19. The process of claim 18, wherein the salmonid is an Atlantic salmon.

20. The process of claim 7, wherein culturing tissue further includes embedding the stem cell tissue in the gel.

21. The process of claim 14, wherein obtaining blood from a fish includes, prior to rendering the fish to a level of loss of reflex activity, reducing the levels of proteolytic enzymes and non-protein nitrogen present in the blood of the fish.

* * * * *